US012667680B2

(12) United States Patent
Aeschlimann et al.

(10) Patent No.: US 12,667,680 B2
(45) Date of Patent: Jun. 30, 2026

(54) INHALER DEVICE FOR INHALABLE LIQUIDS

(71) Applicant: Medical Developments International Limited, Scoresby (AU)

(72) Inventors: Andreas Aeschlimann, Scoresby (AU); Luke Christopher Williams, Scoresby (AU); Scott Cameron Courtney, Scoresby (AU)

(73) Assignee: Medical Developments International Limited, Scoresby (AU)

( * ) Notice: Subject to any disclaimer, the term of this patent is extended or adjusted under 35 U.S.C. 154(b) by 834 days.

(21) Appl. No.: 18/000,611

(22) PCT Filed: Jun. 2, 2021

(86) PCT No.: PCT/AU2021/050545

§ 371 (c)(1),
(2) Date: Dec. 2, 2022

(87) PCT Pub. No.: WO2021/243407

PCT Pub. Date: Dec. 9, 2021

(65) Prior Publication Data

US 2023/0211095 A1     Jul. 6, 2023

(30) Foreign Application Priority Data

Jun. 2, 2020    (AU) ................................. 2020901805

(51) Int. Cl.
*A61M 15/00*          (2006.01)

(52) U.S. Cl.
CPC .... *A61M 15/0086* (2013.01); *A61M 15/0013* (2014.02); *A61M 15/0021* (2014.02); *A61M 15/0036* (2014.02)

(58) Field of Classification Search
CPC .......... A61M 15/0086; A61M 15/0013; A61M 15/0021; A61M 15/0036; A61M 15/0025;
(Continued)

(56) References Cited

U.S. PATENT DOCUMENTS

| | | | |
|---|---|---|---|
| 4,725,442 A | 2/1988 | Haynes | |
| 2010/0083963 A1* | 4/2010 | Wharton | ............. A61M 15/009 |
| | | | 128/203.15 |

(Continued)

FOREIGN PATENT DOCUMENTS

| | | |
|---|---|---|
| CN | 101547717 A | 9/2009 |
| CN | 108348704 A | 7/2018 |

(Continued)

OTHER PUBLICATIONS

Robbins, "Preliminary Studies of the Anesthetic Activity of Fluorinated Hydrocarbons", J Pharmacol Exp Ther, Feb. 1946, pp. 197-204.

(Continued)

*Primary Examiner* — Elliot S Ruddie
(74) *Attorney, Agent, or Firm* — Westman, Champlin & Koehler, P.A.

(57) ABSTRACT

The invention is directed to an inhaler device for inhalable liquids, in particular for the administration of inhalable volatile liquids such as halogenated volatile liquids, to a patient. According to particular embodiments, the inhaler device may include a liquid container for hermetically storing inhalable liquid; a wicking material for supporting inhalable liquid; a piercing member configured to pierce the liquid container, wherein the liquid container may be provided in a first position in which the piercing member does not engage the liquid container and inhalable liquid remains hermetically stored within the liquid container, and the liquid container may be displaced from the first position to (Continued)

a second position such that the piercing member pierces the liquid container to release inhalable liquid onto the wicking material, whereby during inhalation inhalable liquid vapor from the wicking material is delivered to the patient.

18 Claims, 12 Drawing Sheets

(58) Field of Classification Search
 CPC .. A61M 2202/0028; A61M 2202/0241; A61M 2205/75; A61M 2205/7572; A61M 15/06; A61M 2202/0468; A61M 2202/048; A61M 15/004; A61M 15/0016; A61M 15/0018; A61M 15/002; A61M 2205/7536
 See application file for complete search history.

(56) References Cited

U.S. PATENT DOCUMENTS

| | | | |
|---|---|---|---|
| 2018/0007974 A1* | 1/2018 | Thorens | H05B 6/108 |
| 2018/0200459 A1* | 7/2018 | Rowland | A61M 15/002 |
| 2020/0113246 A1 | 4/2020 | Barbaric et al. | |
| 2020/0187560 A1* | 6/2020 | Trzecieski | A24F 40/44 |
| 2021/0177056 A1 | 6/2021 | Yilmaz | |

FOREIGN PATENT DOCUMENTS

| | | |
|---|---|---|
| CN | 109803702 A | 5/2019 |
| CN | 110494049 A | 11/2019 |
| JP | 2018520832 A | 8/2018 |
| JP | 2020078300 A | 5/2020 |
| WO | 1997003711 A2 | 2/1997 |
| WO | 1999034762 A1 | 7/1997 |
| WO | 2002022195 A2 | 3/2002 |
| WO | 2003032890 A1 | 4/2003 |
| WO | 2007033400 A1 | 3/2007 |
| WO | 2008040062 A1 | 4/2008 |
| WO | 2008070490 A2 | 6/2008 |
| WO | 2009094460 A2 | 7/2009 |
| WO | 2009117529 A2 | 9/2009 |
| WO | 2010129686 A1 | 11/2010 |
| WO | 2010129796 A1 | 11/2010 |
| WO | 2010135436 A1 | 11/2010 |
| WO | 2012116187 A1 | 8/2012 |
| WO | 2013016511 A1 | 1/2013 |
| WO | 2013106608 A1 | 7/2013 |
| WO | 2013149263 A1 | 10/2013 |
| WO | 2014143964 A2 | 9/2014 |
| WO | 2015034978 A1 | 3/2015 |
| WO | 2017011865 A1 | 1/2017 |
| WO | 2017011866 A1 | 1/2017 |
| WO | 2017011867 A1 | 1/2017 |
| WO | 2017011868 A1 | 1/2017 |
| WO | 2017205907 A1 | 12/2017 |
| WO | 2018045418 A1 | 3/2018 |

OTHER PUBLICATIONS

Terrell, "The Invention and Development of Enflurane, Isoflurane, Sevoflurane, and Desflurane", Anesthesiology, Mar. 3, 2008, pp. 531-533, vol. 108.

International Search Report and Written Opinion of Corresponding International Application No. PCT/AU2021/050545 dated Jul. 16, 2021.

Office Action in corresponding Chinese Application No. 202180047051.8 dated Sep. 26, 2024.

Office Action in corresponding Japanese application serial No. 2022-574301 dated Nov. 8, 2024.

\* cited by examiner

FIGURE 8F
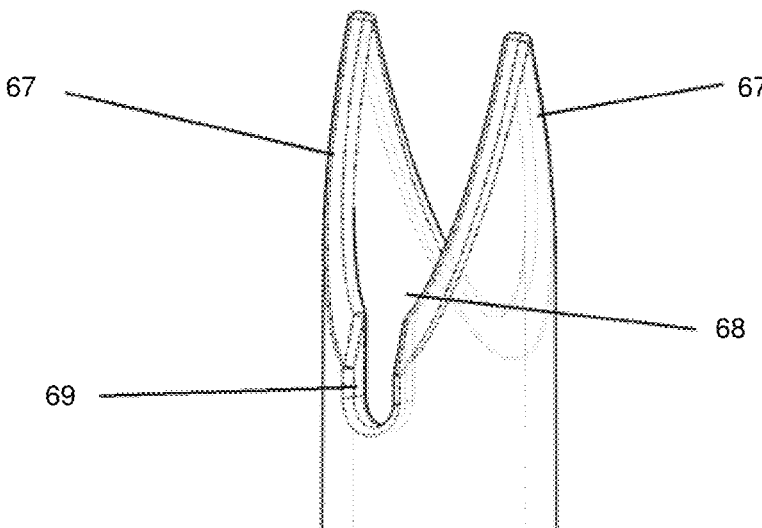
FIGURE 8G
FIGURE 8H
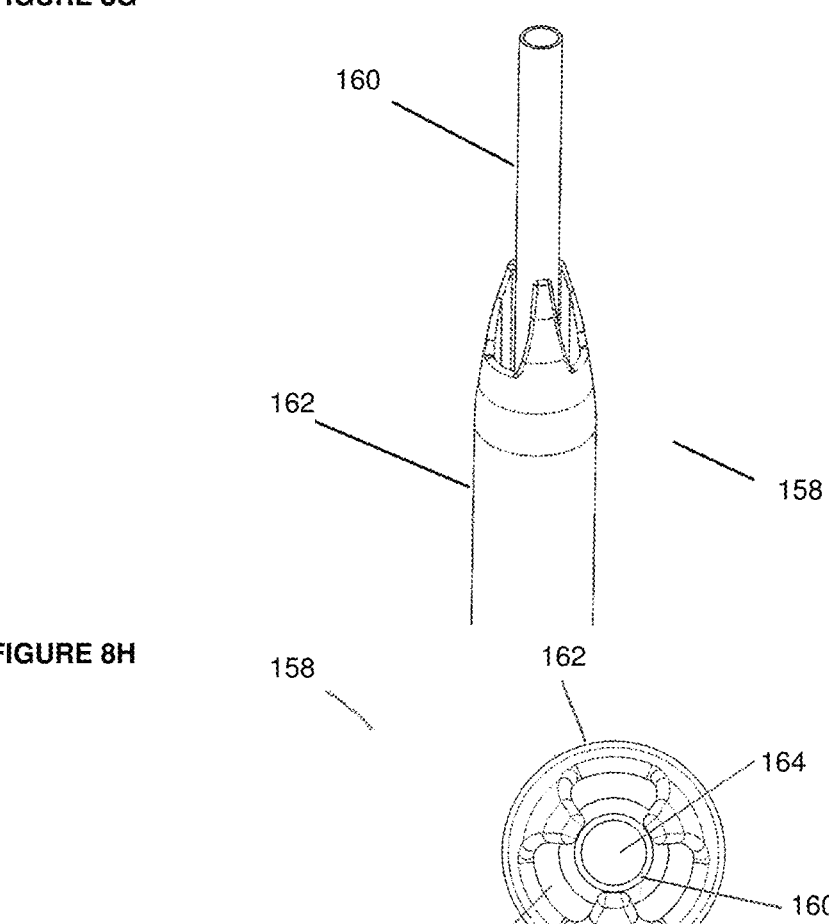

INHALER DEVICE FOR INHALABLE LIQUIDS

CROSS REFERENCE TO RELATED APPLICATION(S)

The present application is a Section 371 National Stage Application of International Application No. PCT/AU2021/050545, filed Jun. 2, 2021 and published as WO 2021/243407 A1 on Dec. 9, 2021, in English, and further claims priority to Australian patent app. Ser. No. 2020901805, filed Jun. 2, 2020.

FIELD

The present invention relates to an inhaler device for inhalable liquids, in particular for the administration of inhalable volatile liquids such as halogenated volatile liquids, to a patient.

BACKGROUND

The storage and administration of inhalable liquids to patients that comprise active agents, or that are themselves the active agent, commonly presents challenges. Active agents such as therapeutic agents or pharmaceutical agents, are often formulated for: oral delivery in the form of tablets and capsules, nasal delivery in the form of sprays, and liquid formulations for intravenous delivery depending on a number of factors.

Where it is advantageous to administer active agents to a patient's lungs, for example to treat or alleviate respiratory diseases, the active agent may be administered by oral inhalation, alone or in combination with the intranasal inhalation. Suitable inhaler devices may include, for example, metered dose inhalers and dry powder inhalers. These types of inhalation devices typically require pressurized means to deliver the active agent to the desired site of action in the lungs. In addition, liquids that contain active agents or that are themselves the active agent usually require transformation into an inhalable, respirational form at the point of administration to be suitable for delivery.

Transforming a liquid into an inhalable form, such as by nebulization or aerosolizing into respirational sized droplets or heating to form a vapor, requires delivery devices to include moving, mechanical, heating and/or electrical means which adds to the complexity of the design, manufacturing and end user costs, the operability and/or patient use.

The use of volatile liquids as active agents or comprising active agents is known. One such example is halogenated volatile liquids. Halogenated volatile liquids have been described as useful for inducing and/or maintaining anesthesia (including amnesia, muscle paralysis, and/or sedation) and/or analgesia and may therefore be useful as anesthetics and/or analgesics. The anesthetic properties of fluorinated compounds have been known since at least 1946 (Robbins, B. H. J Pharmacol Exp Tfter (1946) 86: 197-204). This was followed by the introduction of fluoroxene, halothane and methoxyflurane into clinical use in the 1950s and the subsequent development of enflurane, isoflurane, sevoflurane and desflurane which are in clinical use in some countries today (Terrell, R. C. Anesthesiology (2008) 108 (3): 531-3).

Halogenated volatile liquids, when used for general anesthesia, may be delivered under positive pressure to a patient via a delivery system that includes a vaporizer and a flow of breathable carrier gas. More recently, halogenated volatile liquids have been formulated for use in local or regional anesthesia and delivery via non-inhalation routes. Examples include: formulation as: microdroplets for intradermal or intravenous injection (e.g. U.S. Pat. No. 4,725,442; WO 2014/143964);

compositions suitable for formulation as a solution, suspension, cream, paste, oil, lotion, gel, foam, hydrogel, ointment, liposome, emulsion, liquid crystal emulsion and nanoemulsions for topical, intrathecal, epidural, transdermal, topical, oral, intra-articular, mucosal, buccal, rectal, vaginal, intramuscular, intravesical and subcutaneous delivery (e.g. WO 2008/070490, WO 2009/094460, WO 2010/129686): and stable and injectable liquid formulations (WO 2013/016511).

The main considerations for the safe storage and handling of volatile liquids commonly include vapor pressure build up, the robustness of the container, and the integrity of the container seal(s). The chemical nature of the volatile liquid may also be important if the active agent is capable of permeating, solubilizing or otherwise reacting with the container material(s) upon storage. A number of storage containers for halogenated volatile liquids have been described including:

rigid polymeric containers of various shapes and sizes to replace glass vials, such as: capped bottles, large tanks, and shipping containers (e.g. WO 1999/034762, WO2012/116187);

rigid polymeric bottles fitted with a gasketless valve assembly and pliable containers with a threaded spout for fluid connection to deliver liquid anesthetics to an anesthetic machine or vaporizer (e.g. WO 2010/135436, WO 2013/106608, WO 2013/149263, WO 2015/034978);

a container with a capped membrane for delivering a stored liquid anesthetic to a vaporizer via a slotted tube (WO 2009/117529);

and rigid polymeric and aluminum containers optionally coated with materials to impart or enhance vapor barrier characteristics or container inertness (e.g. WO2002/022195, WO 2003/032890, WO 2010/129796).

Despite the various advances in formulating volatile liquids in non-inhalable forms, such as the halogenated volatile liquids, as well as containers to store them, there still remains a need for inhalable forms of volatile liquids and devices to store and/or administer them to patients.

Attempts to design new inhalers for inhalable medicines in general are ongoing. For example, WO2008/040062 describes a diverse number of inhaler device concepts that depend on complex constructions and moving parts for storing and/or delivering inhalable liquids and powdered solids into a patient's mouth or nose. The various devices described are adapted to hold one or two medicament containers in the form of pressurized canisters, ampoules, vials and plungers. The devices are described as being activated by sliding an outer wall of the device in relation to an inner wall of the device to deliver the liquid medication from a medication container. In a number of embodiments, the device includes a moveable mouthpiece which deploys in order to open the air pathway. The device is also described as including one or more one-way valves to provide a unidirectional air flow for one or both inhaled air and exhaled air (a series of one-way valves to direct the flow of inhaled and exhaled air has also been generally described in WO 2007/033400 which is an incorporation by reference of a device previously described in WO 1997/003711).

When required for use, the devices of WO 2008/040062 are claimed as being capable of releasing the medication by punching means namely two punches to perforate the two respective frangible ends of a medication container, although various other means are generally described including: pressurized means (e.g. by a pressurized canister); frangible means (e.g. by rupturing an ampoule with a striker or by punching a frangible membrane or seal of a vial with punch means); crushable means (e.g. by crushing a vial with a plunger); dislodging means (e.g. by dislodging an unscrewed cap from a vial); and plunging means (e.g. by plunging the medication from the plunger barrel).

However, inhalable liquids such as halogenated volatile liquids require an effective air chamber into which the vapor may evaporate and allow an effective airflow through the air/vapor chamber for delivery to a patient. Accordingly, embodiments such as those described in, for example, FIGS. 48A, 48B, 48C, 49A, 49B, 50A, 50B, 51A, 51B, 56A, 56B, 57, 58A, 58B, 58C and 58D of WO2008/040062, would not be expected to work in practice as the evaporative means (i.e. wick) is prevented from being effectively exposed to effective airflow by the walls of the liquid storage container itself.

Inhaler devices that are useful for administering inhalable liquids may be generally considered to operate by either passive or active means in order to deliver the active agent(s) to a patient. Inhaler devices with active means may include pressurized, moving, mechanical, heating and/or electrical means to, for example, nebulize, vaporize and/or generally deliver the active agent(s). In contrast, inhaler devices with passive means rely solely on the vaporization or evaporation of the active agent(s) at ambient conditions and respiration of the patient to deliver the active agent(s).

The Analgizer™ inhaler device (Abbott Laboratories Corporation) is an example of a device that operates by passive means to deliver an inhalable liquid. According to the USPTO TESS database, the Analgizer™ was a registered, now lapsed, trademark in respect of an inhaler for the supervised self-administration of inhalation anesthesia and was first used in 1968. The Analgizer™ was a very simple device that consisted of a white cylindrical polyethylene open-ended tube having a mouthpiece and an absorbent wick of polypropylene which was tightly rolled into a "Swiss-roll" shape, i.e. cross-sectional view. The inhalation anesthetic, methoxyflurane (15 ml), was poured into the open-ended base of the inhaler and onto the tightly wound wick immediately prior to use. A patient was then able to self-administer the liquid anesthetic by inhaling through the mouthpiece.

The Green Whistle™ inhaler device (Medical Developments International Limited) was subsequently developed during the 1990s and has since been used in Australia for the delivery of methoxyflurane as an analgesic (1.5 mL or 3 mL, storage brown glass vial container with screw cap). Although similar in respect of its simplicity of design to the Analgizer™, the Green Whistle™ device introduced certain functional improvements such as the inclusion of a one-way valve at the base end to prevent drug vapor loss from the device upon patient exhalation and an activated carbon ("AC") chamber designed to be externally fit into a dilution hole in the mouth piece to filter exhaled drug vapors. Additional design modifications to the base end included the introduction of cap lugs to assist removal of the cap from the glass vial used to store the drug dose to be delivered, a dome to facilitate the spread of the poured liquid onto the "S-shaped" wick (cross-sectional view) or, in the alternative to a dome, an inlet nipple to allow for the attachment of a breathable gas line to direct the gas through the device. The Green Whistle™ device is designed for single patient use.

Methoxyflurane (Penthrox®/™, Medical Developments International Limited) offers a non-narcotic, i.e. non-opioid analgesic alternative to common analgesics such as morphine and fentanyl. Methoxyflurane also presents an alternative to analgesics which are administered in oral tablet form or intravenously to a patient and may therefore be particularly useful when rapid pain relief is required in clinical, surgical (e.g. pre- and post-operative) and/or emergency settings (e.g. emergency department and triage management as well as by first-responders such as paramedics and search and rescue teams). However, the Green Whistle™ device is currently the only device that is commercially available to administer methoxyflurane. According to the device's instructions for use, the administrator is required to hold the methoxyflurane bottle upright to use the base of the inhaler to loosen the bottle cap and then to remove the cap by hand before tilting the inhaler to a 45° angle and pouring the contents of the bottle into the base while rotating the device. An AC-chamber may be optionally fitted externally to the device either beforehand or afterwards. While the device is effective, the number of steps and separate components may present handling difficulties for the administrator or self-administrator, for example, in high-stress and/or emergency settings.

The embodiments of the present invention seek to address one or more of the disadvantages identified above, and/or to at least provide the public with a useful alternative.

The reference in this specification to any prior publication or information derived from it, or to any matter which is known is not and should not be taken as an acknowledgement or admission or any form of suggestion that prior publication, or information derived from it, or known matter, forms part of the common general knowledge in the field of endeavor to which this specification relates.

SUMMARY

According to a first aspect of the invention, there is provided an inhaler device for delivering an inhalable liquid to a patient, the inhaler device comprising:

a mouthpiece; an air inlet;

a liquid container for hermetically storing inhalable liquid; a wicking material for supporting inhalable liquid;

a piercing member configured to pierce the liquid container;

a first one-way valve configured to enable gas to flow into the mouthpiece during inhalation, and prevent gas from flowing in the opposite direction during exhalation;

wherein the mouthpiece, first one-wave valve, wicking material, and air inlet are fluidly connected to provide an inhalation chamber; and the inhaler device is configured such that:

the liquid container may be provided in a first position in which the piercing member does not engage the liquid container and inhalable liquid remains hermetically stored within the liquid container;

the liquid container may be displaced from the first position to a second position such that the piercing member pierces the storage container to release inhalable liquid onto the wicking material, whereby during inhalation air entering the air inlet flows through the inhalation chamber to deliver inhalable liquid vapor from the wicking material to the patient via the mouthpiece.

In an embodiment according to the first aspect, the inhaler device further comprises: a return air chamber in fluid communication with a second one-way valve, such that during inhalation the first one-way valve is open and the second one way valve is closed, and during exhalation the first one way valve is closed and the second one-way valve is open to enable exhaled gas to flow from the mouthpiece through the return air chamber.

In an embodiment according to the first aspect, the return air chamber comprises filtering material configured to filter volatile liquid vapor from the exhaled breath of a patient upon exhalation.

In an embodiment according to the first aspect, the filtering material comprises activated carbon, optionally activated charcoal pellets.

In an embodiment according to the first aspect, the liquid container contains a halogenated volatile liquid.

In an embodiment according to the first aspect, the halogenated volatile liquid is selected from the group consisting of halothane (2-bromo-2-chloro-1,1,1-trifluoroethane), sevoflurane (fluoromethyl-2,2,2-trifluoro-1-(trifluoromethyl)ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether).

In an embodiment according to the first aspect, the halogenated volatile liquid is methoxyflurane.

In an embodiment according to the first aspect, the piercing member comprises at least one channel such that, when the liquid container is in the second position, inhalable liquid from the storage container may pass through the at least one channel and onto the wicking material.

In an embodiment according to the first aspect, the wicking material is spaced from the piercing member to allow passage of air through the at least one channel into the liquid container, thereby preventing or reducing an air-lock from restricting release of inhalable liquid from the liquid container.

In an embodiment according to the first aspect, the inhaler device comprises spacer tabs configured to space the wicking material from the piercing member.

In an embodiment according to the first aspect, the wicking material and/or the piercing member remains stationary within the inhaler device while the liquid container is displaced from the first position to the second position.

In an embodiment according to the first aspect, the liquid container comprises only a single region configured to be pieced.

In an embodiment according to the first aspect, the inhaler device is configured to enable air to pass by or around the liquid container, optionally the inhaler device is configured to prevent air from passing through the liquid container.

In an embodiment according to the first aspect, the inhaler device comprises a diluter hole positioned to enable a portion of inhalation air to bypass the wicking material before passing into the mouthpiece.

In an embodiment according to the first aspect, the diluter hole is positioned and configured to enable the patient to restrict or block the diluter hole with a finger.

In an embodiment according to the first aspect, the mouthpiece comprises a filter configured to reduce or prevent inhalation of liquid droplets by the patient.

In an embodiment according to the first aspect, the filter is formed of a polymeric non-woven material.

In an embodiment according to the first aspect, the inhaler device is configured to enable replacement of the liquid container and/or the wicking material.

In an embodiment according to the first aspect, the wicking material is configured to enable inhalation air to pass through and along multiple surfaces of the wicking material, optionally the wicking material is configured to enable inhalation air to pass through and along a first surface and a reverse surface of the wicking material.

The present summary is provided only by way of example and not limitation. Other aspects of the present invention will be appreciated in view of the entirety of the present disclosure, including the entire text, claims, and accompanying figures.

Definitions

Throughout this specification and the claims which follow, unless the context requires otherwise:

terms such as "side", "end", "top", "bottom", "above", "below", and the like are only used to describe elements as they relate to one another, but are in no way meant to recite specific orientations of the device, to indicate or imply necessary or required orientations of the device, or to specify how the invention described herein will be used, mounted, displayed, or positioned in use:

"active agents" refers to therapeutic agents and non-therapeutic agents and compounds, formulations and compositions comprising them, and "active agent" has a corresponding meaning;

"air" or "gas" may be used interchangeably;

"alleviate", "alleviations" and variations thereof refers to relieving, lessening, reducing, ameliorating or an improvement in the symptom(s) and/or underlying cause(s) of a condition and/or disease in a patient:

"comprise" and variations thereof such as "comprises" and "comprising", will be understood to imply the inclusion of a stated integer or step or group of integers or steps but not to the exclusion of any other integer or step or group of integers or steps:

"delivery dose" refers to the dose of inhalable liquid or active agent for administration to a patient;

"filter", "filtering" and variations thereof refers to the ability of a substance to absorb, adsorb, capture, trap, scavenge, scrub or partially or entirely remove the inhalable volatile liquid vapor from the exhaled breath of a patient upon exhalation:

"halogenated volatile liquids" refers to volatile liquids which (i) comprise at least one halogen atom selected from the group consisting of a chlorine (Cl), bromine (Br), fluorine (F) and iodine (1) atoms, or (ii) comprise an active agent which comprises at least one halogen atom selected from the group consisting of a chlorine (Cl), bromine (Br), fluorine (F) and iodine (1) atoms. In some embodiments, halogenated, particularly fluorinated, hydrocarbons and halogenated, particularly fluorinated, ethers may be preferred. In some embodiments, halogenated ethers may be particularly preferred and include but are not limited to, halothane (2-bromo-2-chloro-1,1,1-trifluoroethane), sevoflurane (fluoromethyl-2,2,2-trifluoro-1-(trifluoromethyl) ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether);

"inhalable liquid" refers to liquids that comprise active agents or that are themselves the active agent and that are readily inhalable or capable of being or adapted to be inhaled by a patient. In some embodiments, inhalable volatile liquids, particularly halogenated volatile liquids are preferred;

"inhalation", "inhalable" and variations thereof refers to the intake of, for example but not limited to air, breathable gases, inhalable liquids, by a patient and includes both oral and nasal inhalation. In some embodiments, oral inhalation is particularly preferred:

"and/or" means "and" and "or" where the context allows for both;

"patient" refers to both human and veterinary patients. In some embodiments, human patients may be particularly preferred. Reference to a patient will therefore be understood to mean the person or animal to whom the inhalable liquid is administered to and in the case of human patients, will be understood to include administration by self-administration;

"pharmaceutical agent" refers to a drug, or a compound, formulation or composition that comprises a drug, for the treatment of symptom(s) and/or underlying cause(s) of a condition and/or disease in a patient. The term pharmaceutical agent may be used interchangeably with therapeutic agent or active agent;

"respiratory", "respirational" and variations thereof refers to the act of respiring, breathing, inhaling and exhaling, such as for example but not limited to air, breathable gases, inhalable liquids and active ingredients, by a patient;

"room temperature" refers to ambient temperatures which may be, for example, between 10° C. to 40° C. but more typically between 15° C. to 30° C.:

"therapeutic agent" refers to an active agent, or a compound, formulation or composition (including biological compounds, formulations and compositions) that comprises an active agent, that is capable of treating a patient or offers a therapeutic or medical benefit to a patient or that has or that requires regulatory and/or marketing approval for therapeutic use in a patient. Therapeutic agents include pharmaceutical agents. In contrast, a 'Non-therapeutic agent' will be understood to mean an active agent which may not have or require regulatory and/or marketing approval for a therapeutic use such as, for example, smokeless tobacco products and electronic cigarettes, or does not have a recognized or identified therapeutic use but may be used by a patient for a non-therapeutic reason such as general health, wellbeing or physiological benefit such as, for example, nutraceutical products.

"treat", "treatment" and variations thereof refers to the alleviation, modulation, regulation or halting of the symptom(s) and/or underlying cause(s) of a condition and/or disease in a patient. In some embodiments treatment may include preventative or prophylactic treatment and "volatile liquids" refers to substances that predominantly exist in a liquid form but readily form vapors, evaporate or vaporize such that they partially exist in a vapor form under ambient conditions for example, at room temperature and at normal atmospheric pressures.

BRIEF DESCRIPTION OF THE FIGURES

FIG. 8F shows a further embodiment of an opener in accordance with the present invention.

FIGS. 8G and 8H show a further embodiment of an opener in accordance with the present invention.

Figure 1A:
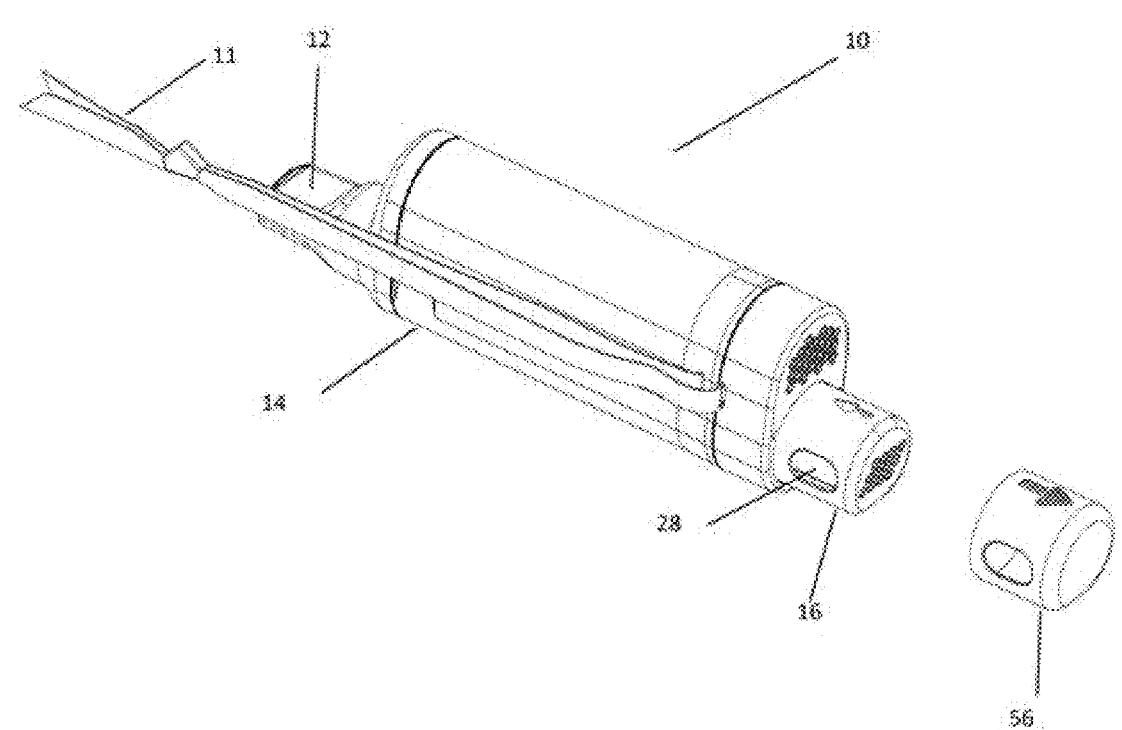
FIGS. 1A and 1B show an external view of an inhaler device having a fluid container in a first position and a second position respectively according to an embodiment of the invention.

While the above-identified figures set forth one or more embodiments of the present invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features, steps, and/or components not specifically shown in the drawings.

LIST OF COMPONENTS

10—inhaler device
11—hand strap
12—mouthpiece
14—body
16—receptacle
18—liquid
20—cartridge
22—opener
23—projection
24—chamber
26—fluid pathway
28—window
30—wicking material
31—voids
32—holder
34—valve assembly
34a—valve support
34b—valve plate 36—receiver
38—dock
40—air inlet
42—apertures
44—diluter hole
50—exhalation chamber
52—adsorbent material
54—exit ports
56—end cap
58—chamber body
60—filter assembly
64—filter
70—slotted guides
72—recessed portion
74—central raised portion
76—recessed portion
80—spacer tabs
100—cannula
101—piercing member
102—bore
104—cannula
105—piercing member
106—bore
108—cannula
110—bore
120—vial
122—closure
130—vial
132—screw-type closure
133—aperture
134—membrane
140—closure
142—plug
150—tab
152—ridge
158—piercing member
160—hollow shaft
162—flow member
164—ventilation path
166—channels
180—diluter hole
182—mouthpiece

DETAILED DESCRIPTION

In broad terms, the present invention relates to a new inhaler device for the administration of inhalable liquids to a patient, such as halogenated volatile liquids, particularly methoxyflurane for use as an analgesic. The present invention is now further exemplified with reference to embodiments as set out below and in the drawings.

EMBODIMENTS

Embodiments of the invention will now be described with reference to the non-limiting examples.

Figure 1B:
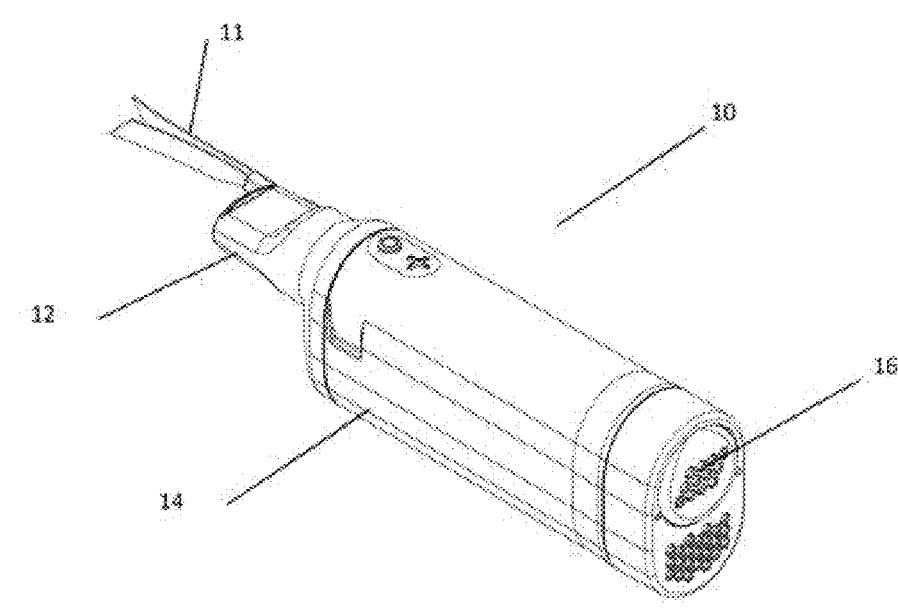

In accordance with a first embodiment, FIGS. 1A and 1B shows an inhaler device 10 having a hand strap 11, mouthpiece 12, a body 14, a receptacle 16 and end cap 56 in a first position and a second position respectively. In the first position shown in FIG. 1A, the receptacle 16 projects from the body 14 of inhaler device 10, and may be covered by an end cap 56. In FIG. 1B, the receptacle 16 has been moved to a second position where the receptacle 16 has moved into body 14 of inhaler device 10 as described below.

Figure 2A:
FIGS. 2A and 2B show a cross-sectional cut-away view of the device of FIG. 1A along line A-A with the fluid container in the first position.
Figure 2B:
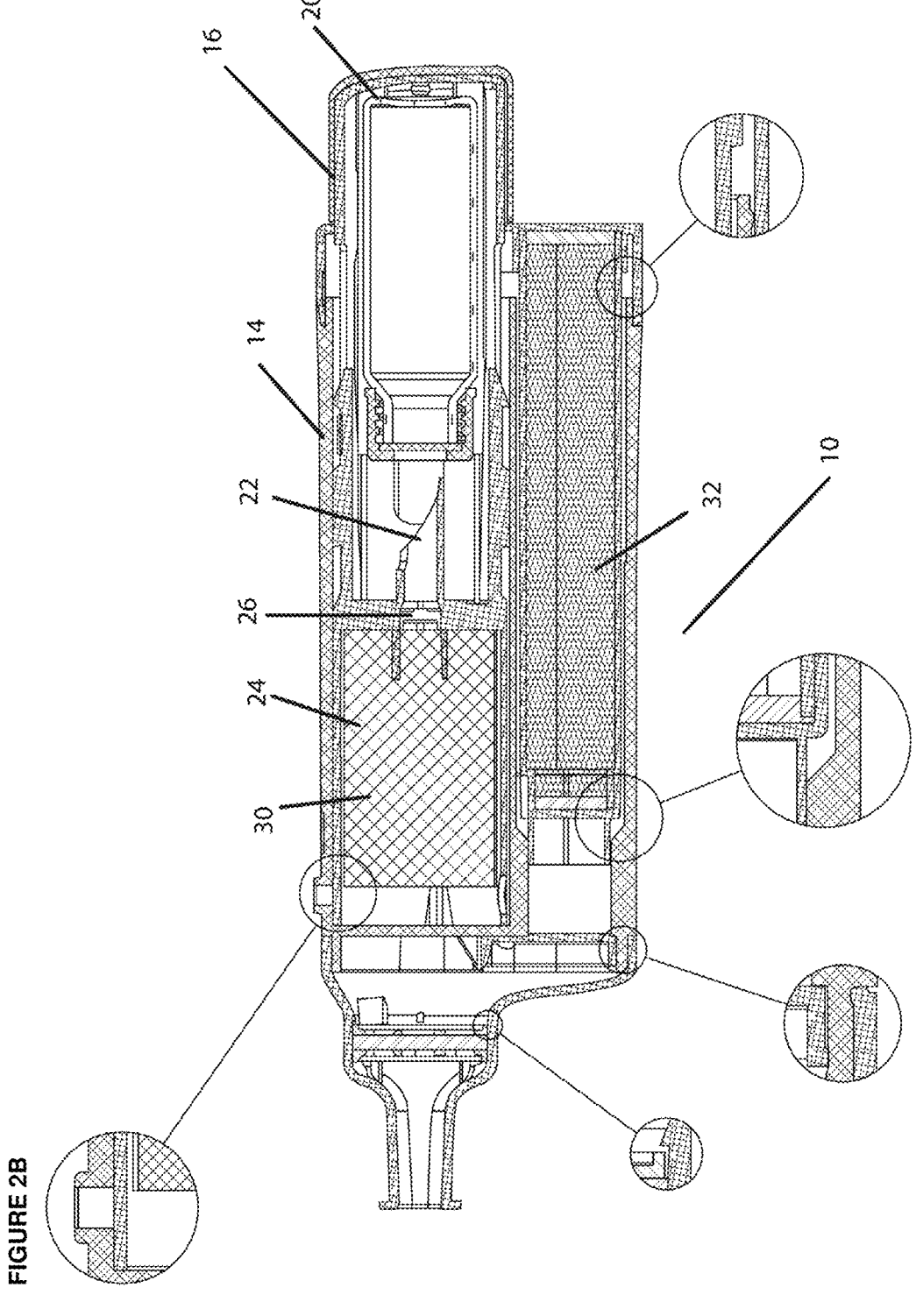

Further detail of the inhaler device 10 is shown in FIGS. 2A and 2B, where receptacle 16 is shown in the first arrangement, housing a cartridge 20 partially within the body 14 of the inhaler device 10. The cartridge 20 may hold a fluid, for example a liquid 18, such as a volatile liquid, such as methoxyflurane. Also within body 14 is an opener 22 connected to a chamber 24 by fluid pathway 26. Chamber 24 may include a wicking material 30.

Figure 5:
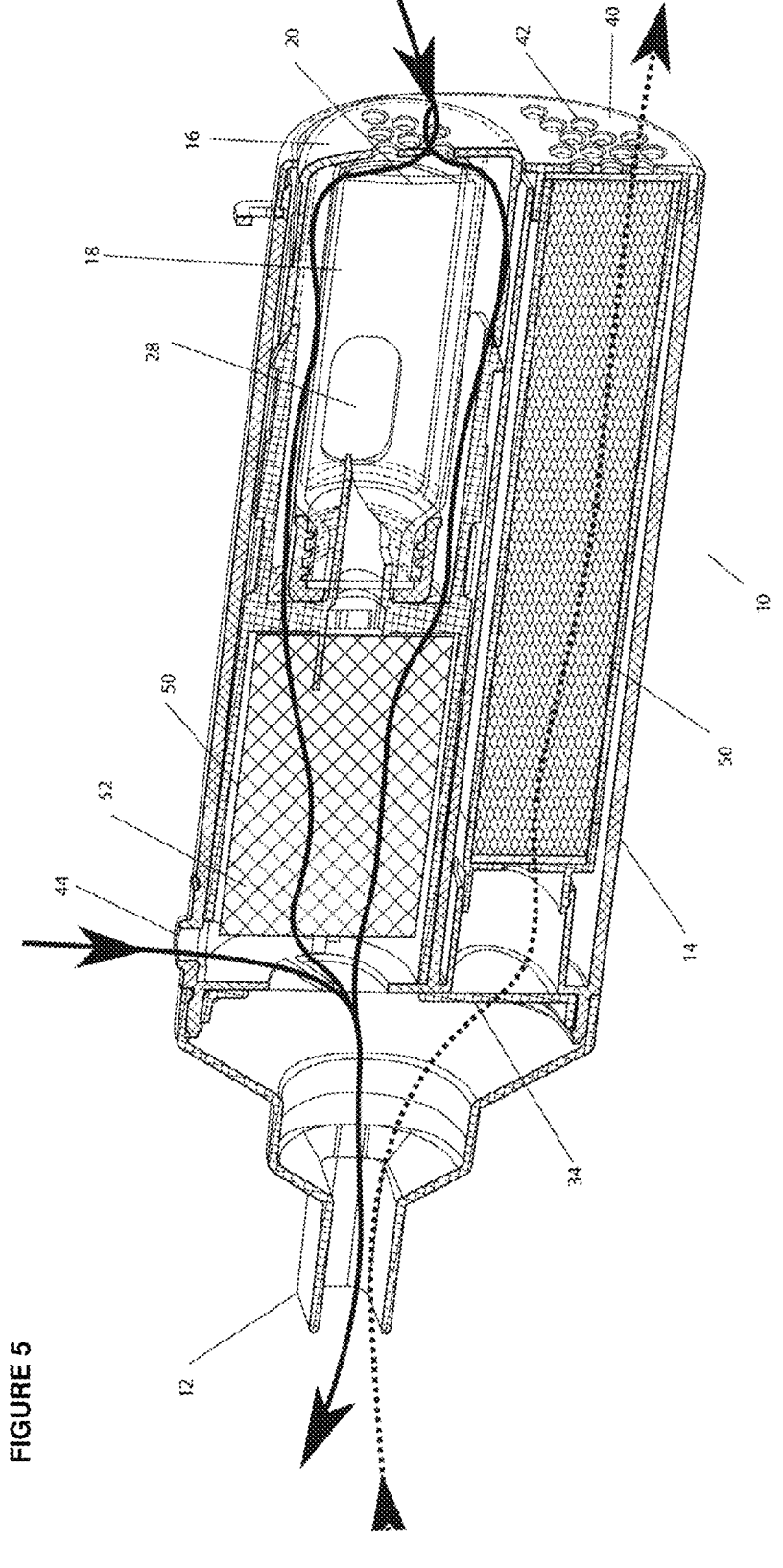
FIG. 5 shows a cross section of the inhaler device in FIG. 1B with the fluid container in a second position, indicating airflows within the device in use.

In FIGS. 1A and 2B, the cartridge 20 is located within the receptacle 16, such that air may flow around the cartridge 20, through receptacle 16 and into chamber 24. Examples of air flow are as shown in FIG. 5. In other embodiments (not shown) the receptacle 16 and cartridge 20 may be integral with each other, for example molded from a single piece. In other embodiments (not shown) the air flow to the chamber 24 may be around the receptacle 16, through the cartridge 20 or separate to the receptacle 16 and cartridge 20 entirely.

Figure 3:
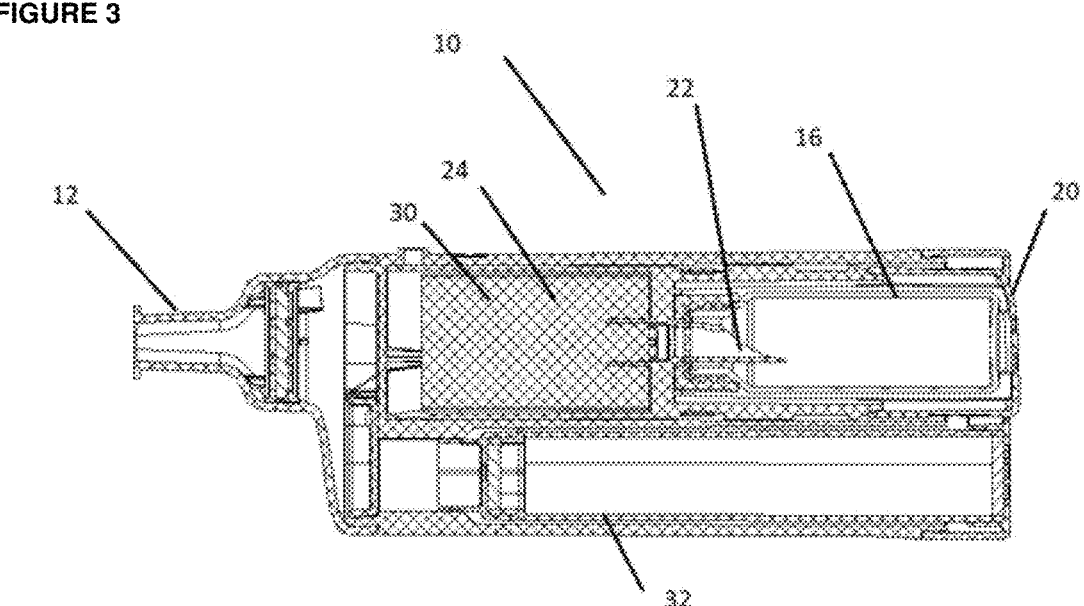
FIG. 3 shows a cross-sectional cut-away view of the device of FIG. 1B along line B-B with a fluid container in the second position.
Figure 4:
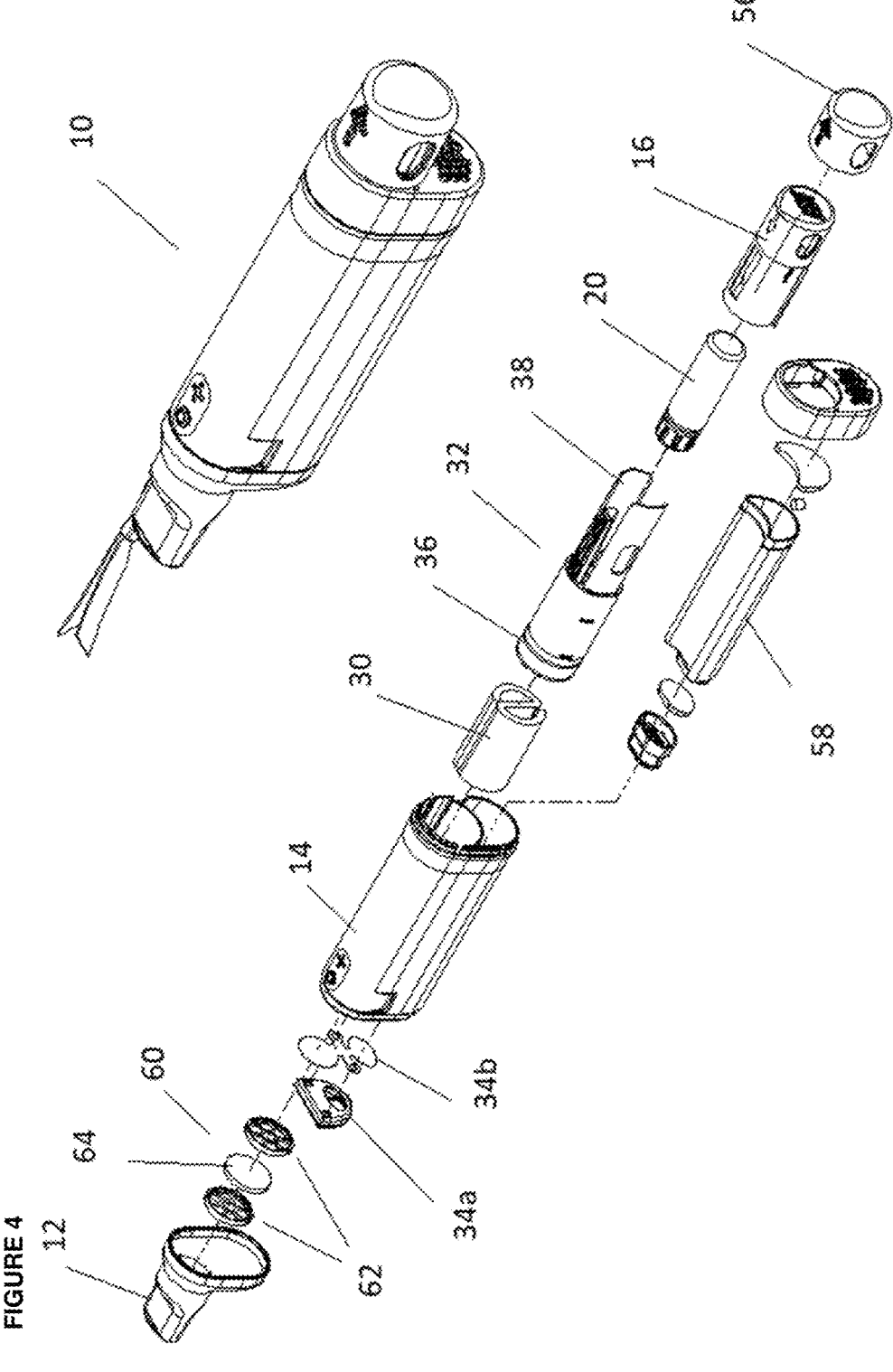
FIG. 4 shows a disassembled view of the inhaler device of FIG. 1A.

As shown in FIG. 4, the cartridge 20 may be loaded into the receptacle 16 during assembly or manufacture of the finished inhaler 10. The cartridge 20 may be a vial, such as a glass walled 5 ml vial having a screw on lid. The lid may have a pierceable portion, such as a butyl rubber section with allow permeability polymer coating such as a PTFE coating to assist in sealing in volatile liquids such as methoxyflurane. FIG. 2 shows the receptacle 16 and cartridge 20 in the first position, where the opener 22 has not engaged the cartridge 20. FIGS. 1B, 3 and 5 show the receptacle 16 and a cartridge 20 in a second position where the opener 22 has engaged the cartridge 20 to release liquid 18.

The embodiments shown and described herein are adapted to dispense liquid that is capable of vaporizing at room temperatures in sufficient amounts to be medically effective and not require storage pressure to assist in dispensing the liquid to the patient.

Receptacle 16 may include a window 28 allowing visual inspection of the contents of the cartridge 20. If cartridge 20 is transparent, such as a glass or plastic vial, the level of liquid remaining in cartridge 20 will be visible, to determine the level of liquid in the cartridge 20 prior to opening to determine whether all the liquid 18 has been dispensed from the cartridge 20.

In FIG. 4 cartridge 20 fits into receptacle 16 during assembly. Receptacle 16 holding cartridge 20 is loaded into a holder 32. Holder 32 incorporates a number of elements, including a receiver 36 for wicking material 30, and a dock 38 for receptacle 16. The dock 38 allows the receptacle 16 to move from the first position to the second position by engaging with the receptacle 16 as described below.

Figure 9A:
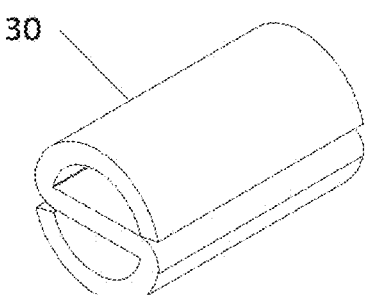
FIGS. 9A and 9B show different views of a wicking material in accordance with the inhaler device of FIG. 1A.
Figure 9B:
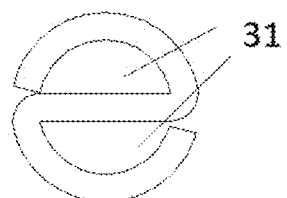

Wicking material 30 may be provided according to various, different configurations. In the embodiment shown in FIG. 9, wicking material 30 is shown as a single piece in an S-shape, such that wicking material 30 is generally located along the walls of receiver 36, and across the center of receiver 36. Within the receiver 36, wicking material 30 has voids 31 that allow the free passage of air, which picks up vapor from liquid 18 evaporating on the wicking material 30, where it exits the receiver 36, which in use is located in chamber 38 within body 10 as shown in FIGS. 3 and 5.

According to the present embodiment the wicking material 30 is securely held in the receiver 36 of holder 32 to ensure that the orientation and arrangement of the wicking material 30 is consistent and stable. Wicking material 30 may be made of a variety of materials such as a polypropylene felt or sintered polypropylene, to provide appropriate wicking with the liquid such as methoxyflurane. When assembled, the inhaler devices may be packed and stored for some time before use and the wicking material may not have significant strength. Further, inhaler device 10, may be used in a variety of locations, and be subject to rough handling prior to use. It is envisaged that the inhaler device 10 may be used in a variety of environments, including in moving ambulances, in military operations, or situations in the field outside a hospital environment. As such, locating device as described below may be employed to retain the wicking material in its preferred location.

Figure 10:
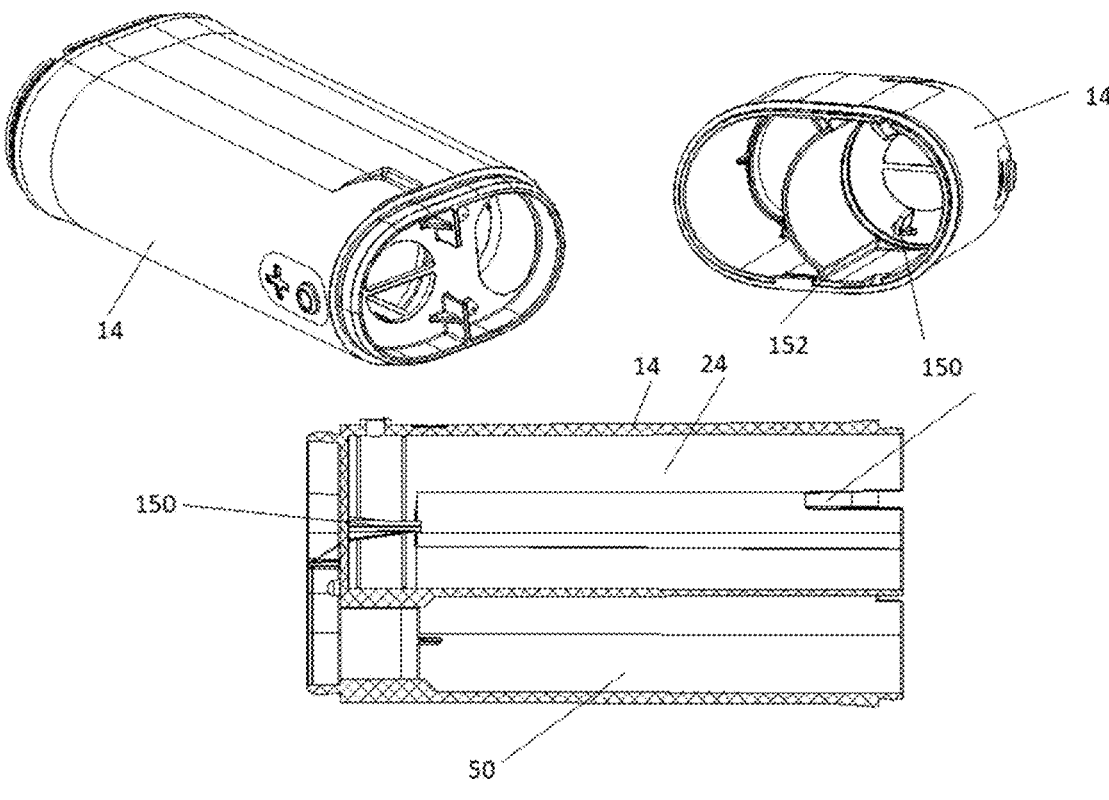
FIG. 10 shows different views of sections of the body of the inhaler device of FIG. 1B.

FIG. 10 shows different views of the body 14 of the inhaler device 10. Specifically, the end of the body 14 proximal the mouthpiece 12. Tab 150 inside the body 14 assists in locating the wicking material 30, at opposite ends of the body 14 to the tabs 80, which also assist in locating the wicking material 30. Optionally, a ridge 152 may run along all or part of the inside of the body 14 in chamber 24 to prevent movement, such as rotation, of the wicking material within the chamber 24.

According to certain embodiments of the inhaler device 10, air flow through the wicking material 30 and any gaps or voids 31 after dispensation of liquid 18 onto wicking material 30 is consistent to provide a repeatable air/vapor ratio. Unlike purely liquid analgesics, the operation of analgesics such as methoxyflurane is dependent on the ratio of vapor of active pharmaceutical ingredient to air. If too little vapor is inhaled, the therapeutic effect may not be sufficient. The importance of the user being able to control or adjust the concentration or delivery of the active pharmaceutical ingredient is discussed below.

Figures 11A, 11B, 11C, 12:
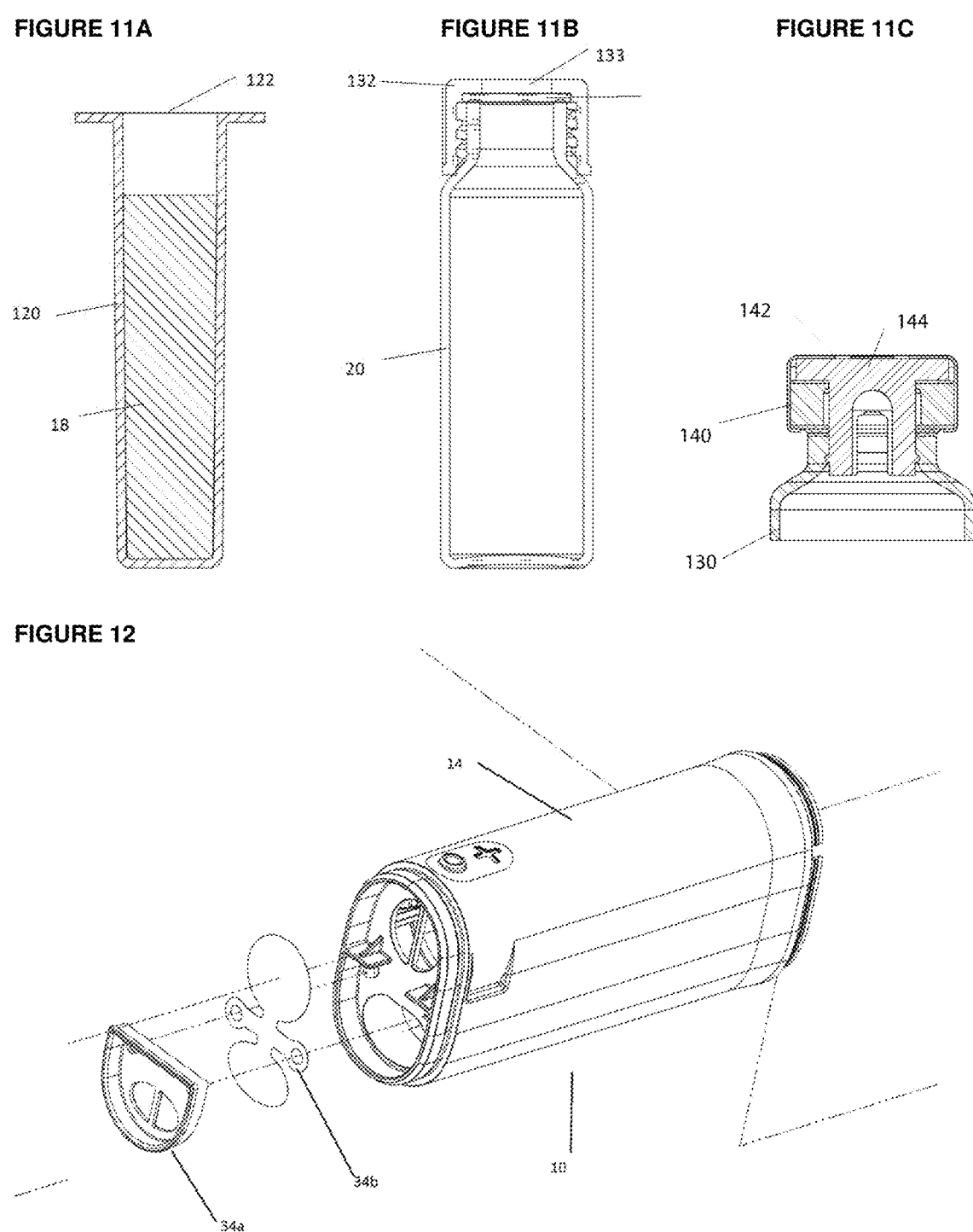
FIGS. 11A, 11B and 11C show different embodiments of cartridges and closure mechanisms in accordance with the present invention.
FIG. 12 shows an isometric view of a valve arrangement of the inhaler device of FIG. 1A.

The receptacle 16 is moveable from a first position shown in FIGS. 1A and 2, to a second position shown in FIGS. 1B and 3 to release liquid 18. The cartridge 20 is locked into position with and moves when the receptacle 16 is moved, and opener 22 moves to pierce or penetrate a pierceable portion of the cartridge 20 as shown in FIGS. 3 and 5. Different embodiments of cartridges and pierceable portions are shown in FIGS. 11A, 11B and 11C and described below. If the inhaler device 10 is held substantially vertically or at an incline with the mouthpiece 12 held lowermost, liquid 18 within the cartridge 20 will then move from the cartridge 20 through a pierced aperture in a closure 132 shown in FIG. 11B through fluid pathway 26 and into chamber 24 where it will be absorbed by wicking material 30. According to the embodiment shown, the wicking material 30 is of such a volume that not all the spaces within it are filled with fluid, some air remains as described above.

Different configurations of cartridge are shown in FIGS. 10A, 10B and 10C. A vial 120 is shown in FIG. 11A having a closure 122 that may be attached via heat or ultrasonic welding. The closure 122 may be a piece of plastics material chosen to weld easily to the vial 120, be pierceable and be impermeable to the liquid 18

Cartridge 20 shown in FIG. 11B has a screw type closure 132, for example made of a stiff plastics material. The top of the closure 132 may contain an aperture 133, and a membrane 134 may be placed within the closure to fit between the closure 132 and cartridge 20 when the closure is applied. The closure 132 may be screwed to the top of the cartridge 20, holding the membrane 134 tightly against the cartridge 20 to prevent leakage during storage prior to use. The membrane 134 may be pierceable via a cannula style piercing member as shown as opener 22 in FIGS. 2B and 3.

An additional embodiment is shown in FIG. 11C where a cartridge such as a vial 130 (only the top of which is shown) has a crimp style closure 140 having a plug 142 fitting under the closure 140 and accessible through aperture 144. During assembly, the vial 130 is filled with liquid, and the closure 140 containing plug 142 is fitted to the vial 130 where the edges of the closure 140 are crimped around edges of the vial 130. The plug 142 is held tightly between the closure

140 and vial 130 to provide a seal. The plug 142 is made from a pierceable material such as butyl rubber, and may incorporate an additional impermeable membrane (not shown) if required. In each case described and shown in FIGS. 10A, 10B and 10C, a closure method is described that is pierceable and retains liquid during storage.

In use, a patient may place their mouth over the mouthpiece 12 and inhale air, drawing it through the inhaler device as shown in FIG. 5. Air enters air inlet 40 through, for example apertures 42, then around cartridge 20 and into chamber 24 where it interacts with fluid 18 in wicking material 30. Wicking material 30 supports the liquid 18 and provides a large surface area interface between liquid 18 and air, such that air flowing through the wicking material 30 picks up vapor from the fluid 18. When fluid 18 is a volatile fluid such as methoxyflurane, the vapor level can be high enough to produce a therapeutic response in the person inhaling the air through the inhaler device 10. In order to allow the patient to vary the concentration of the air/vapor mix, a diluter hole 44 is provided in the body 10, which provides air containing no vapor direct to the mouthpiece. A patient can fully or partially block the diluter hole 44, such as with their finger, to adjust the concentration of vapor in the air exiting the mouthpiece 12 into the patient. Uncovering diluter hole 44 dilutes the vapor in the air by allowing air that has not passed through the receiver 36 to enter the inhaler device 10 before inhalation by a patient.

Figure 13:
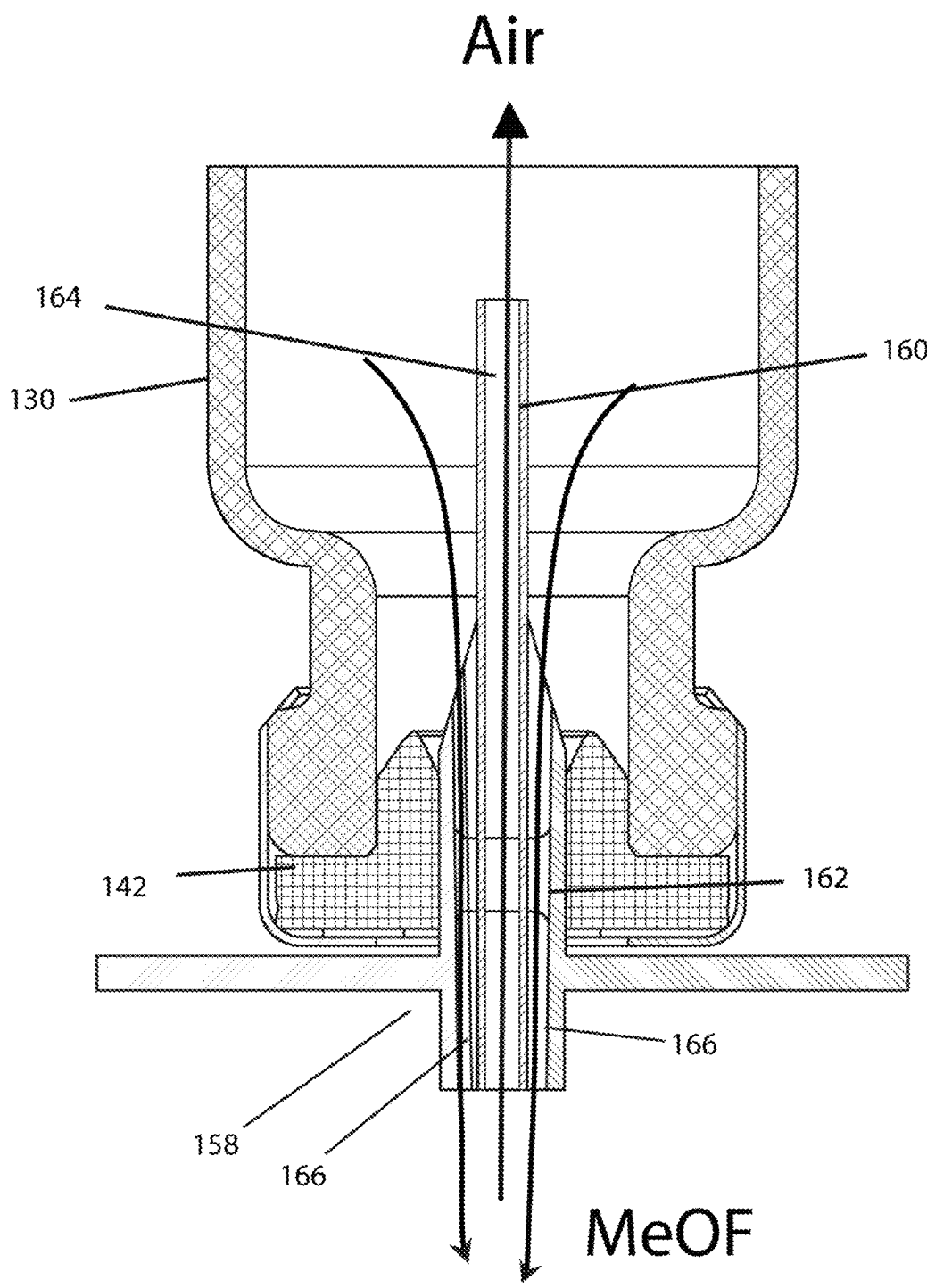
FIG. 13 shows a cross sectional view of the opener of FIGS. 8G and 8H.

In another embodiment of the inhaler device 10 shown in FIG. 13, the diluter hole 180 is placed at the end of the device adjacent mouthpiece 182. This embodiment allows easier placement of a one-way valve (not shown) such as a reed valve, to prevent exhaled air from leaving the deice except through the chamber 50.

Exhaled air from a patient will contain some remaining vapor which was not absorbed by the patient. The patient may exhale air back into the mouthpiece, whereupon the valve assembly 34 (new FIG. 4 will require simple description of parts) directs the air containing remaining vapor, into exhalation chamber 50 as shown in FIGS. 3 and 5. Chamber 50 may contain an adsorbent material 52 such as an activated charcoal to adsorb vapor remaining in exhaled air. Exhaled air exits the inhaler device from exit port 54. A parts view of Chamber 50 is shown in FIG. 4, wherein a chamber body 58 is used to house adsorbent material 52 such as activated charcoal pellets and ensure no leakage of air into the body 10. Chamber 50 allows the retaining absorbent material separate to other parts of the inhaler device 10 during assembly.

In some embodiments (not shown) the chamber 50 is not required and the patient may breathe out normally not into the device. Valve assembly 34 would still prevent air flow from returning back through the chamber 24.

Figure 6:
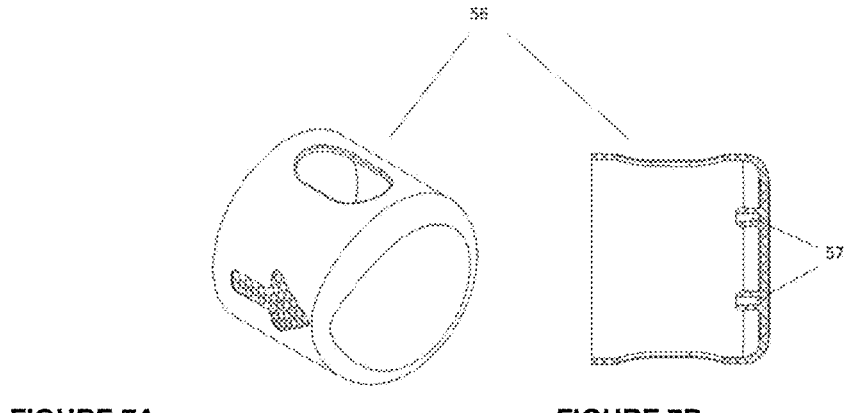
FIG. 6 shows an isometric and cross-sectional view of an end cap of the inhaler device of FIG. 1A.
Figure 7A:
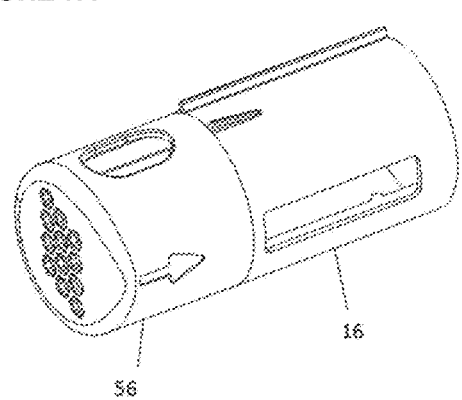
FIGS. 7A and 7B show an isometric view of an end cap and receptacle of the inhaler device of FIG. 1A.
Figure 7B:
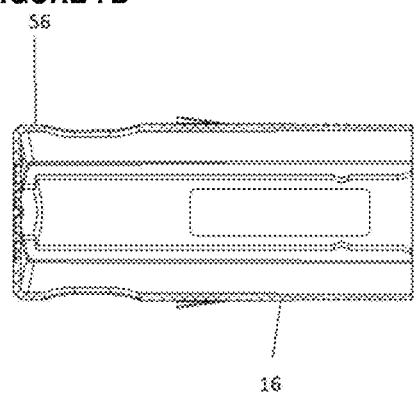

In one embodiment shown in FIG. 6, an end cap 56 is provided to engage with and cover the end of receptacle 16 when the receptacle 16 is in a first position as shown in FIG. 1. In one form the end cap 56 engages with the receptacle by, for example, interference projections 57 to positively engage the receptacle 16 and prevent it from moving to the second position shown in FIGS. 3 and 5 until end cap 56 is removed.

In use the end cap 56 must be removed, to expose the receptacle 16, whereupon a patient may then move the receptacle to the second position, and in the process, the opener 22 engages with closure (number and pictures) to pierce the closure and release liquid 18 as herein described. This has significant advantage over prior art methods that had a separate vial, for example when trying to open the liquid container and pour it onto the wicking material in a moving vehicle such as an ambulance.

Optionally, as shown in FIG. 4, a filter assembly 60 is shown including filter holders 62 either side of filter 64. The filter assembly 60 is located on the mouthpiece side of valve assembly 34. This prevents foreign material from entering the inhaler device 10 and potentially interfering with the valve assembly 34. Filter assembly 60 also prevents material that may be held within the inhaler device 10, being inhaled by a patient. The filter 64 may be a non-woven material or other suitable material. It may also prevent droplets of liquid 18 from entering the mouth or airways of a patient, rather than as a vapor mixed with air. Such materials as polypropylene may be used.

Figure 8:
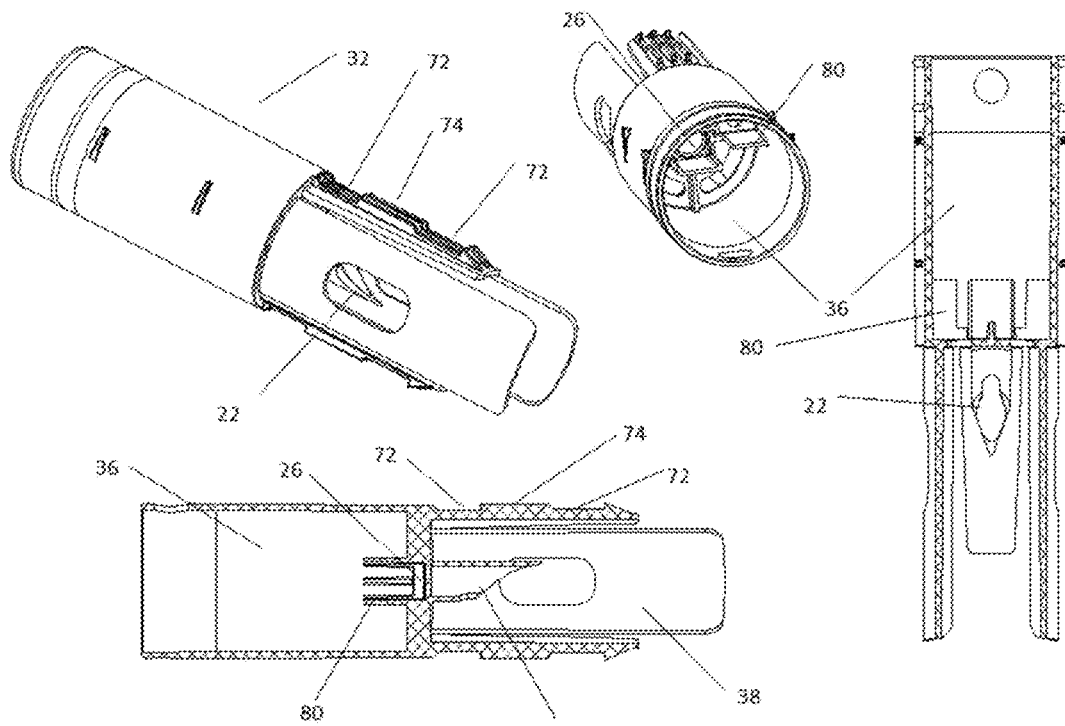
FIG. 8 shows isometric and cross-sectional views of a holder for an inhaler device as shown in FIG. 1A.

FIG. 8 shows multiple views of an embodiment of holder 32. Holder 32 includes opener 22, receiver 36 for receiving receptacle 16 (not shown) dock 38 for receiving wicking material 30 (not shown) and slotted guides 70. Slotted guides 70 have two recessed portions 72 which define the first and second position of the receptacle 16. The central raised portion 74 between the two recessed portions 76 as shown in Figure BE provides a positive resistance to the receptacle moving to the second position without a minimum force being exerted. Further, once in the second position, the central raised portion prevents the receptacle sliding away from the opener, and possibly preventing full discharge of the liquid into the wicking material 30.

Also shown in FIG. 8 are spacer tabs 80 within the receiver 36 of holder 32. Spacer tabs 80 ensure that an air gap exists between the wicking material 30 and the fluid pathway 26. This assists in ensuring liquid 18 spread around wicking material 30, the cartridge 20 is appropriately vented to prevent an air lock preventing liquid draining from the cartridge, and that air can flow freely over wicking material 30 and through receiver 36. This provides better drainage of the cartridge 20 and provides a more consistent air to vapor mix from initial opening of the receptacle 16 until most of the liquid has vaporized into the air flow though the inhaler device 10. Spacer tabs 80 also ensure that the wicking material 30 is held securely in place.

Figures 8A, 8B, 8C, 8D, 8E:
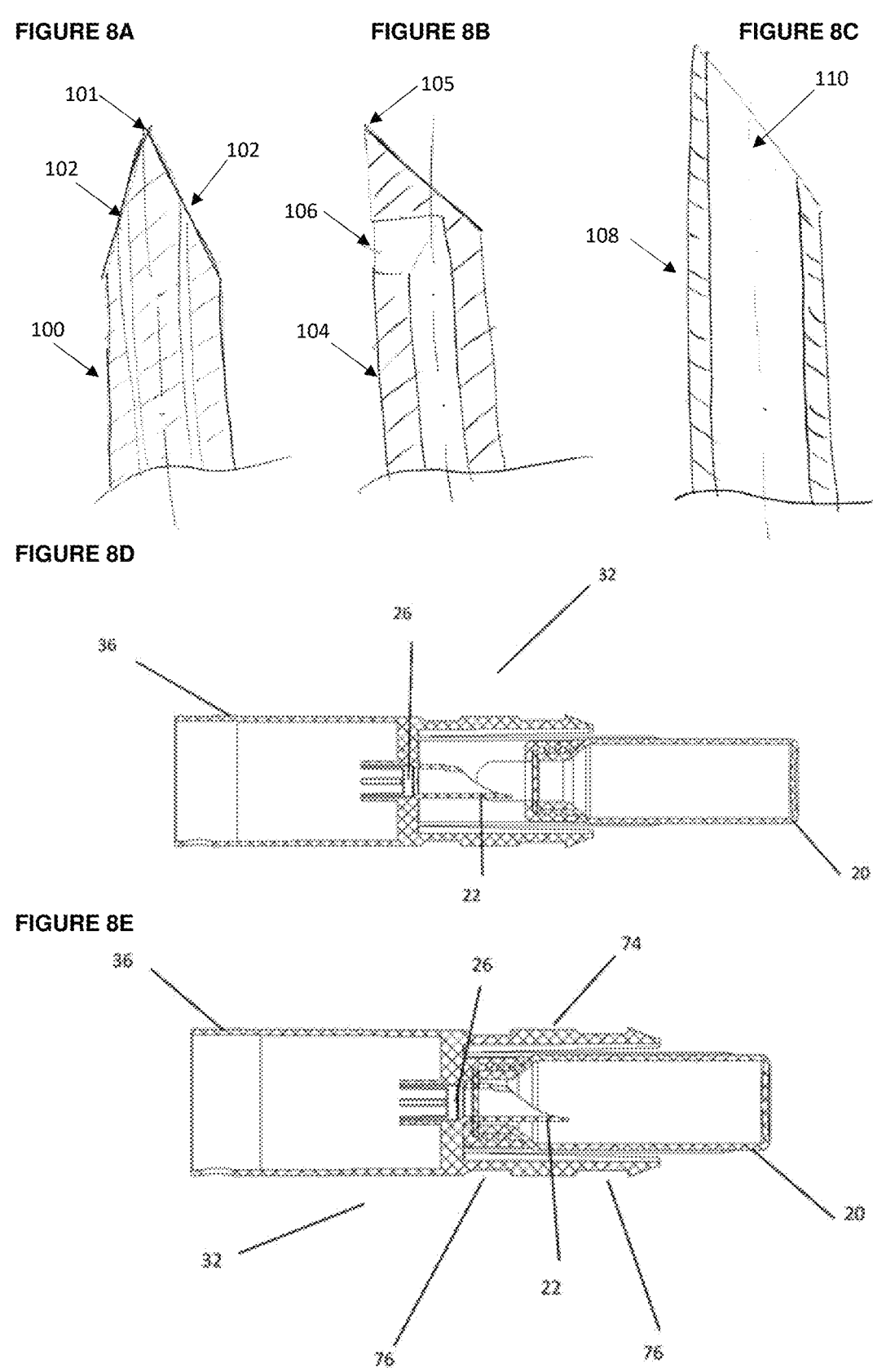
FIGS. 8A, 8B and 8C show different embodiments of an opener in accordance with the present invention.
FIGS. 8D and 8E show the receptacle in the first position in accordance with the inhaler device of FIG. 1 and the second position in accordance with the inhaler device of FIG. 1B respectively.

Opener 22 is shown as one embodiment of a piercing member in FIG. 2B and FIG. 3 with additional embodiments shown in FIGS. 8A, 8B and 8C. In FIG. 8 the opener 22 is shown with an aperture 22A and a projection 23. Projection 23 is designed to pierce pierceable members of cartridges such as those shown in FIGS. 10A, 10B and 10C.

In FIG. 8A, a cannula 100 is shown having a piercing member 101 and bores 102. Although two are shown distal from the end of piercing member 101, multiple bores 102 maybe used.

In FIG. 8B, piercing member 105 is offset from the centerline of cannula 104 and bore 106 exits from the side of the cannula 104.

In FIG. 8C, cannula 108 has a single large bore 110. In the embodiments shown, the arrangements of the bore in relation to the cannula are adapted to reduce the chance of the pierceable member blocking the bore and preventing liquid from draining from the cartridge. In some cases, it has been found that draining of liquid from cartridges can be incomplete or blocked if the bore of the piercing member is blocked. Opener 22 has an aperture to increase the size of the opening, and the other embodiments place the bore or bores in locations that have reduced risk of blockage. The choice of embodiment is dependent on the type of closure used on the cartridge.

In FIG. 8F, a further embodiment of an opener 66 is shown. Opener 66 has two piercing members 67 surrounding a fluid channel 68 which connects to fluid pathway 26 (not shown). A slot 69 is located between piercing members 67. In use, when the cartridge 20 such as that shown in FIG. 11B, is moved from a first position to a second position, the piercing members 67 pierce membrane 134 such that the piercing members 67 move into the cartridge 20 but that the membrane 134 does not extend past the slot 69. The piercing members are designed to cut a round section from membrane 134. The slot 69 allows a fluid pathway around the round section, should it get caught between the piercing members 67 and otherwise block fluid channel 68.

In FIGS. 8G and 8H, a piercing member 158 is shown having a hollow shaft 160 supported in a flow member 162. The hollow shaft may be made from metal and be in the form of a blunt needle having a ventilation path 164, adapted to pierce for example the plug 142 of vial 130. The flow member 162 may be constructed from a plastics material and have a number of flow channels 166 to allow flow of liquid from the vial 130 to the wicking material. FIG. 13 shows the piercing member piercing the plug 142 wherein air may flow into the vial 130 to assist in release of liquid (in this case MeOF, or Methoxyflurane) through the flow channels 166. This is advantageous where the liquid is stored in vials that are not pressurized, and therefore liquid may not flow easily if there is not an air channel.

An embodiment of the one-way valve 34 is shown in FIG. 12 consisting of a support 34a and flexible valve plate 34b. Flexible valve plate 34b has a lobe covering the air pathway to the chamber 24 housing the wicking material 30 and another lobe covering the return air pathway to exhalation chamber 50. Differences in air pressure each side of the lobes will cause deflection and allow air to flow thus creating a one-way valve for each chamber 24 and 50 respectively. Support 34a is located on the opposite side of the valve plate 34b to form the seal when air is inhaled. This embodiment provides a simple but effective seal using two easily assembled parts.

The wicking material 30 may be made from any material that is suitable for absorbing the inhalable liquid and passively releasing it as a vapor. Wicking properties will generally be understood to include the ability of a material to facilitate or enhance the rate of evaporation or vaporization of a liquid from its surface by distributing the liquid, whether by drawing, spreading, pulling or otherwise, throughout the material from its initial point of contact and/or as it evaporates from an exposed surface area of the material. The wicking material should incorporate a large surface area to volume ratio to assist in ensuring good vaporization of the liquid into the surrounding air. In one embodiment the wicking material is a wicking felt or a porous polymeric material. In a preferred embodiment the wicking material is a polypropylene wicking felt. In another embodiment, a sintered polypropylene material may be used.

Figure 14:
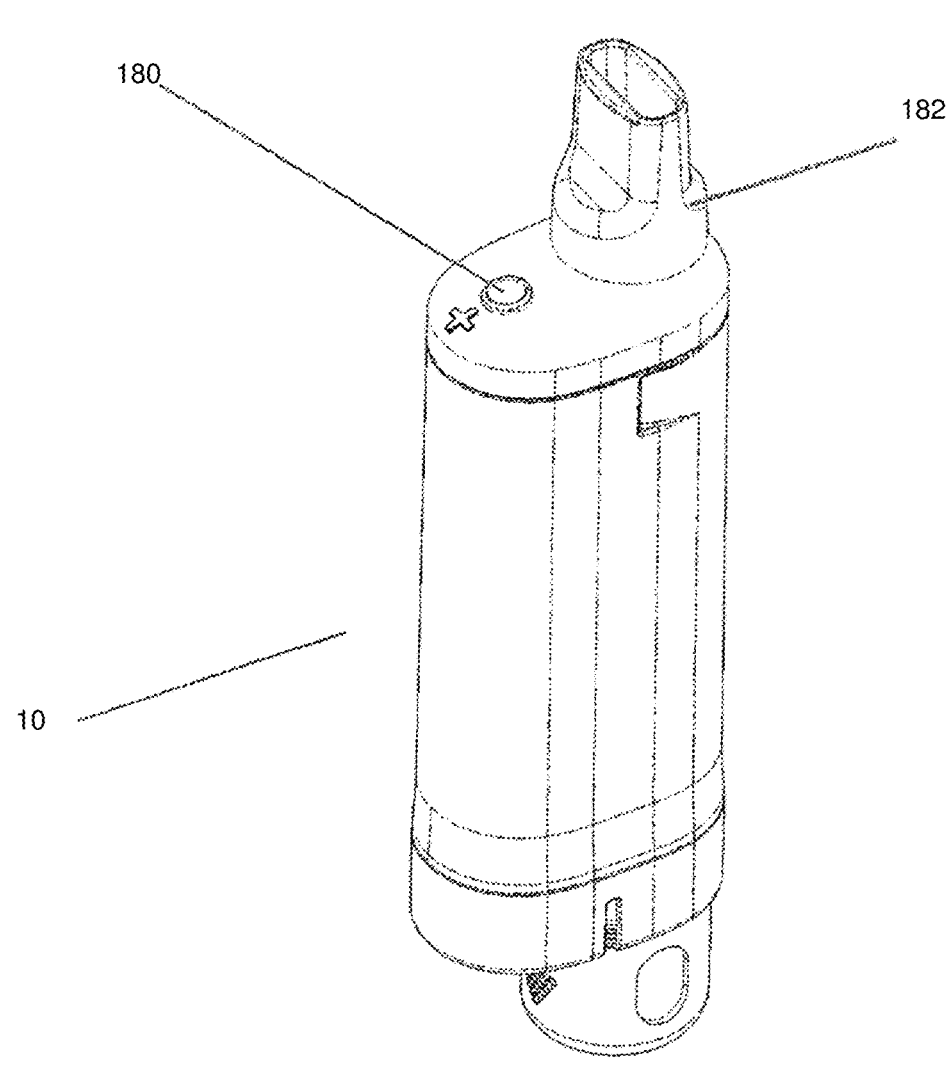
FIG. 14 shows a further embodiment of the inhaler device.

The inhaler device described in various embodiments herein has a benefit that the ratio of active pharmaceutical ingredient may be varied by the patient/user by a number of means. Firstly, the user may control the concentration of active pharmaceutical ingredient by covering the diluter hole 44 or 180 in FIG. 14 to increase the concentration (reducing additional airflow bypassing the wicking material 30) or by leaving the diluter hole fully or partially open, to allow air to mix with the air and vapor flowing through the receiver 36 and wicking material 30.

Additionally, the user does not need to only breath in air from the inhaler device 10. The user may inhale through the inhaler device 10 one or more times to obtain relief, then when breath normally. Active pharmaceutical ingredients such as Methoxyflurane will provide analgesia for many minutes after inhalation, so if a user is in pain, the inhaler device 10 is designed to be held and controlled by them, to manage their own pain. This also allows the user to communicate during the process of taking the analgesic, in such circumstances where medical professionals may be assessing the injuries of the user or other information.

It will be understood to persons skilled in the art of the invention that modifications may be made without departing from the spirit and scope of the invention. The embodiments or examples as described herein are therefore to be considered as illustrative and not restrictive.

The invention claimed is:

1. An inhaler device for delivering an inhalable liquid to a patient, the inhaler device comprising:

a mouthpiece;

an air inlet;

a liquid container for hermetically storing inhalable liquid;

a wicking material for supporting inhalable liquid;

a piercing member configured to pierce the liquid container, the piercing member comprising one or more fluid channels arranged to enable liquid to drain from the liquid container through the piercing member; and a first one-way valve configured to enable gas to flow into the mouthpiece during inhalation, and prevent gas from flowing in the opposite direction during exhalation; wherein the mouthpiece, the first one-wave valve, the wicking material, and the air inlet are fluidly connected to provide an inhalation chamber; and the inhaler device is configured such that:

the liquid container may be provided in a first position in which the piercing member does not engage the liquid container and inhalable liquid remains hermetically stored within the liquid container;

the liquid container may be displaced from the first position to a second position such that the piercing member pierces the liquid container to release inhalable liquid onto the wicking material through the piercing member, whereby during inhalation air entering the air inlet flows through the inhalation chamber to deliver inhalable liquid vapor from the wicking material to the patient via the mouthpiece; and the wicking material is spaced from the piercing member to allow passage of air through the at least one channel into the liquid container, thereby preventing or reducing an air-lock from restricting release of inhalable liquid from the liquid container.

2. The inhaler device according to claim 1, and further comprising: a return air chamber in fluid communication with a second one-way valve, such that during inhalation the first one-way valve is open and the second one way valve is closed, and during exhalation the first one way valve is closed and the second one-way valve is open to enable exhaled air to flow from the mouthpiece through the return air chamber.

3. The inhaler device according to claim 2, wherein the return air chamber comprises filtering material configured to filter volatile liquid vapor from the exhaled breath of a patient upon exhalation.

4. The inhaler device according to claim 3, wherein the filtering material comprises activated carbon.

5. The inhaler device according to claim 1, wherein the liquid container contains a halogenated volatile liquid.

6. The inhaler device according to claim 5, wherein the halogenated volatile liquid is selected from the group consisting of halothane (2-bromo-2-chloro-1,1,1-trifluoroethane), sevoflurane (fluoromethyl-2,2,2-trifluoro-1-(trifluoromethyl)ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether).

7. The inhaler device according to claim 6, wherein the halogenated volatile liquid is methoxyflurane.

8. The inhaler device according to claim 1, wherein the inhaler device comprises spacer tabs configured to space the wicking material from the piercing member.

9. The inhaler device according to claim 1, wherein the wicking material and/or the piercing member remains stationary within the inhaler device while the liquid container is displaced from the first position to the second position.

10. The inhaler device according to claim 1, wherein the liquid container comprises only a single region configured to be pieced.

11. The inhaler device according to claim 1, wherein the inhaler deviceis configured to enable air to pass by or around the liquid container.

12. The inhaler device according to claim 1, wherein the inhaler device comprises a diluter hole positioned to enable a portion of inhalation air to bypass the wicking material before passing into the mouthpiece.

13. The inhaler device according to claim 12, wherein the diluter hole is positioned and configured to enable the patient to restrict or block the diluter hole with a finger.

14. The inhaler device according to claim 1, wherein the mouthpiece comprises a filter configured to reduce or prevent inhalation of liquid droplets by the patient.

15. The inhaler device according to claim 14, wherein the filter is formed of a polymeric non-woven material.

16. The inhaler device according to claim 1, wherein the inhaler deviceis configured to enable replacement of the liquid container and/or the wicking material.

17. The inhaler device according to claim 1, wherein the wicking material is configured to enable inhalation air to pass through and along multiple surfaces of the wicking material.

18. The inhaler device according to claim 1, wherein the inhaler device is configured prevent air from passing through the liquid container.

* * * * *